United States Patent [19]

Haarasilta et al.

[11] Patent Number: 5,314,692

[45] Date of Patent: May 24, 1994

[54] ENZYME PREMIX FOR FEED AND METHOD

[75] Inventors: Asko N. O. Haarasilta, Vantaa; Pirkko L. A. Riikonen, Kirkkonummi; Leo Vuorenlinna, Helsinki, all of Finland

[73] Assignee: Cultor Ltd., Helsinki, Finland

[21] Appl. No.: 697,920

[22] Filed: May 2, 1991

Related U.S. Application Data

[63] Continuation of Ser. No. 88,675, Aug. 24, 1987, abandoned.

[51] Int. Cl.[5] .................. A61K 37/62; A61K 37/54; C12N 11/02
[52] U.S. Cl. .................. 424/94.2; 424/94.3; 424/94.6; 424/94.61; 424/94.63; 435/174; 435/177; 435/178; 435/188
[58] Field of Search .............. 435/174, 177, 178, 188; 424/94.1, 94.2, 94.3, 94.6, 94.61, 94.63

[56] References Cited

U.S. PATENT DOCUMENTS

| | | | |
|---|---|---|---|
| 3,868,448 | 2/1975 | Hahn et al. | 424/94.62 |
| 3,880,742 | 4/1975 | James et al. | 435/200 |

FOREIGN PATENT DOCUMENTS

| | | | |
|---|---|---|---|
| 1201384 | 3/1986 | Canada | 424/94.1 |
| 113626 | 7/1984 | European Pat. Off. | 435/188 |
| 104324 | 6/1984 | Japan | 424/94 |

*Primary Examiner*—Jacqueline Stone
*Attorney, Agent, or Firm*—Baker & McKenzie

[57] ABSTRACT

A thermostable premix for use in animal feeds which comprises a carrier material onto which an enzyme solution containing enzymes which are not inherently heat stable are absorbed.

6 Claims, 1 Drawing Sheet

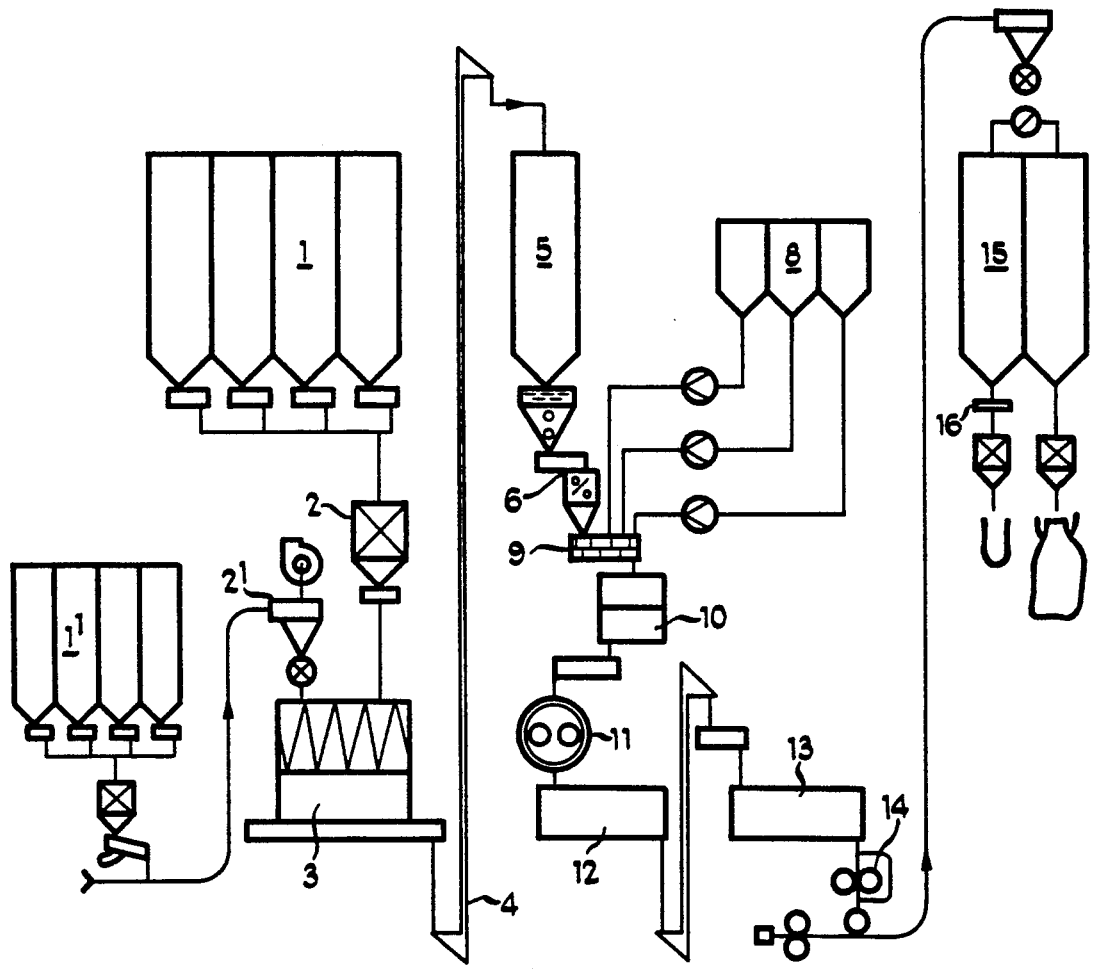

ENZYME PREMIX FOR FEED AND METHOD

This application is a continuation of application Ser. No. 088,675, filed Aug. 24, 1987 now abandoned.

TECHNICAL FIELD

This invention relates to a feed premix, containing one or more enzymes, which is dry, thermally stable and easy to mix and handle. More particularly the invention relates to a dry, thermally stable premix which comprises a physiologically acceptable carrier in combination with one or more enzymes, and a method for producing such a premix.

BACKGROUND OF THE INVENTION

The use of enzymes to treat animal feed mixes is well known. The treatment of animal feed mixes with enzymes can improve the digestibility of the feed and hence making the feed more efficient and increase its energy content. For example, Hollenbeck in U.S. Pat. Nos. 2,988,949 and 2,988,448 describes the treatment of raw barley feed with barley malt containing cytolytic enzymes; Hollenbeck reports that poultry fed with the treated feed showed improved growth rate because of the increased energy value of the feed. In general, enzymes act to break down feed products, thus increasing the availability of digestible components in the feed to the animal.

However, despite the numerous advantages enzymes have as feed additives, their use in feeds is limited by several drawbacks. One particular problem is the heat instability of most enzymes. It is well known that temperatures approaching 100° C. will in virtually all cases deactivate (permanently) enzymes, and most enzymes will be deactivated if exposed to temperatures approaching 70° C. The heated conditions under which most feed processing takes place inctivates any enzymes present. Elevated temperatures are a characteristic of modern feed processing techniques. In typical feed pelleting processes, the feed is usually "preconditioned" with steam for ten seconds to about three minutes which elevates the temperature to about 70°-80° C. The preconditioning step is followed by pelleting of the feed which takes place at temperatures in the range of 80°-85° C. Other feed processing techniques involve longer "conditioning" and the feed is held at elevated temperatures (60°-95° C.) for periods of five to three minutes. These temperatures (in combination under certain conditions with elevated pressure levels) tends to deactivate unprotected enzymes, even those which may be inherently thermostable. Moreover, the amounts of enzymes which need to be added are extremely small making effective and uniform mixing a serious problem. The difficulty in utilizing enzymes as a feed ingredient is also exacerbated by the fact that mos commercial enzyme products are enzyme solutions which are more difficult to mix than dry ingredients.

One possible solution to these problems is the utilization of pre-mix. Because ingredients such as antibiotics, vitamins, minerals and the like are added to the feed in small quantities, they cannot be added directly to the feed because uniform distribution would be impossible in the context of commercial feed production. A premix consisting of a carrier and active ingredients is generally utilized to introduce these "micro-ingredients" into the feed. Hiller, in U.S. Pat. No. 4,218,437 discloses the use of a feed premix wherein the active ingredients consist of antibiotics in combination with certain enzymes. However, Hiller does not disclose or suggest that the premix discussed could be effectively and efficiently utilized in the large scale commercial production of feed.

Feed premixes—for effective utilization in commercial feed processing—must have certain properties including, inter alia, physical stability, non-interference with the chemical stability of the active product, and good flow and blending properties. To date, no such feed premix containing enzymes has been available for large scale use.

In sum, it has not been simple or cost effective to use enzymes as a feed additive on a large commercial scale.

This invention, however, provides for a relative dry, thermally stable premix which contains one or more enzymes which can be utilized for commercial feed processing. The premix has a high enzyme activity which is not significantly affected by high temperatures used in feed processing "which typically range from about 70°-95° C.". This premix has good flow properties and can be easily and uniformly blended into a feed mixture to effectively improve the properties of the feed.

SUMMARY OF THE INVENTION

The present invention contemplates a relatively dry, thermally stable enzyme premix which consists essentially of a physiologically acceptable carrier and one or more enzymes. The premix has a good flow and blending properties and can be easily and uniformly blended into feed. The carrier consists of a physiologically acceptable feed ingredient which is compatible with the active enzyme ingredients; preferred carriers include grain flours such as wheat and barley.

The invention also contemplates a method for making an enzyme-feed premix by mixing a physiologically acceptable carrier with one or more enzymes, reacting the admixture so that the enzyme or enzymes are substantially absorbed into the carrier and then pelletizing, drying and milling the resulting product. The premix product preferably has a moisture content of less than about 10%. The enzyme can be added as a dry ingredient or as part of an enzyme solution. This method produces an enzyme premix which is thermally stable and does not exhibit any significant degradation of the enzymes at feed processing temperatures.

BRIEF DESCRIPTION OF THE DRAWING

In the Drawing, a production line for the preparation of the enzyme premix is depicted.

DETAILED DESCRIPTION OF THE PREFERRED EMBODIMENT

A. General

We have found that the stability of enzymes in feed processing is greatly increased by the preparation of an enzyme premix wherein the enzyme is absorbed onto a carrier consisting of flour or other similar material, and pelletized. The resulting thermally stable premix has good flow properties and can be easily blended into a feed mixture to final concentrations of about 0.01–0.5% by weight. The premix can be easily blended into feed in amounts of less than 5 kg premix per ton of feed. The carrier is preferably prepared from a suitable, natural starch-containing material such as grain or flour and typically the carrier may itself contain several active enzymes.

Pelletizing the enzyme/carrier improves the thermal stability of the active enzyme or enzyme ingredients present. Pelletization also makes it possible to dry the premix product to a water content below about 30% by weight; preferably the water content is between about 7% and about 15% by weight with a particularly preferred water content of less than about 10% by weight. Drying of the premix in the context of this invention does not significantly denature or deactivate the enzyme or enzymes present. The pelletized premix is easily dried by warm air at a temperature below 65° C., preferably below 45° C. The dried pellets can be crushed or milled before mixing with the final feed mixture.

The premix contains an enzyme and/or enzyme combinations which improve the qualities of the feed mixture. Such enzymes include, inter alia, starch hydrolyzing enzymes or amylases, cellulose hydrolyzing enzymes or cellulases, cellulose hydrolyzing enzymes or cellulases and hemicellulases, glucanases, lipases, proteinases and the like. In particular, suitable enzymes include cellulases from *Thircoderma reesei* or proteases from *Bacillus subtilis*, which are usually marketed as enzyme solutions, or dry products like the alpha-amylase prepared from *Bacillus subtilis*. The enzymes are generally present in a liquid form although dried enzyme product can also be utilized.

The carrier material can be any physiologically acceptable feed ingredient which is compatible with the active enzyme ingredients. The preferred carrier material is a suitable flour product which permits an enzyme solution to be mixed with the carrier without drying of the enzyme. If an enzyme solution is utilized, additional water does not generally need to be added prior to pelletization because the enzyme-water solution provides the required moisture. Of course, dry enzymes can also be added to the mixture, along with water, instead of or in addition to enzyme solutions.

Suitable carriers include starch containing flours, for example wheat, barley or other grain flour, which have water contents of less than about 15% by weight, with a preferable water content of about 12% to about 14%. The carrier generally comprises between about 40% to about 99% by weight of the premix with a preferable concentration between about 40% to about 90%. The enzyme or enzymes generally comprise about 1% to about 60% of the premix by weight, with a preferable content of about 10% to about 40%.

The present invention contemplates an enzyme feed premix, and method for production of such a premix, which can be used for large scale commercial feed production. The FIGURE depicts a preferred embodiment for an apparatus to produce such an enzyme in this context.

The FIGURE depicts an effective and efficient production line for the preparation of an enzyme premix. The carrier materials from storage silos (1) and (1¹) are weighed on the balance (2) and transferred to the mixer (3). The transporter (4) transfers the mixed carrier materials to the storage silo (5). From the storage silo (5) the carrier materials are transferred to the balance (6) and weighed together with dry enzyme products. Enzyme solutions are stored in tanks (8) and are transferred in the appropriate amount(s) to the mixer (9) for mixing. A suitable mixer is a continuous type mixer, for example, an Amandus Kahl "Durchlaufmischer Grösse Type 12 III" or similar device. Steam is added to the mixer if necessary to increase the moisture content of the mix. From the mixer the enzyme-carrier mixture is transferred to a reaction tank (10) where the enzymes are absorbed into the carrier material. A suitable reaction tank is the Amandus Kahl type LK 2210-2 tank or a similar device, which is equipped with an agitator. In the absorption tank the mixture remains for 10–60 minutes, typically for approximately 30 minutes.

Thereafter the mixture is fed to a suitable pelletizing device (11) for example, an Amandus Kahl types 35-780 pelletizer (or similar collar-type device) where the material is pressed through a matrix and the formed stripes are cut into suitable pellets with a length of approximately 15 mm and diameter of about 5–8 mm. The moisture of the mass when arriving into the pelletizing machine is generally between about 18% and about 19% and the temperature is kept below about 60° C., preferably below about 45° C.

After pelletization the product is dried with warm air (12) in a drying medium such as the Amandus Kahl 275-04 band-drier or a similar drying device. Finally the product is cooled (13) so that the final moisture content is approximately 8%. The dry, cool pellets can be crushed or milled (14). From the crusher oversize particles are returned while the product is transferred to the storage silos (15). The product is finally treated in a centrifugal machine which disintegrates the particles and homogenizes the product. A suitable device for this purpose is the Simon Entoleter Standard IMP 590 "sentry impact infestation destroyer" or similar devices. The resulting product is ready for packaging and shipping.

The enzyme premix prepared from this method exhibits thermal stability and is free flowing, easy to handle and easily blended. The low moisture content of the premix—preferably less than about 10% by weight—contributes to these properties. In addition, the process outlined above results in a premix with a relatively high enzymatic activity, because the methods employed do not significantly affect the activity of the added enzyme.

One advantage of the present invention is that it allows enzyme solutions to be used in place of dry products. Enzyme solutions are generally cheaper than corresponding dry products contributing to the overall price efficiency of the instant method.

B. Experimental

Example 1

A premix intended for poultry feed was prepared from the following ingredients:

|  | Weight % |
| --- | --- |
| Wheat flour | 78.9 |
| alpha-amylase | 1.5 |
| Protease | 1.1 |
| Cellulase with beta glucanase | 18.5 |

The product was prepared according to the method depicted in the FIG. 1 and described above in part A. This premix was relatively dry, stable and free flowing with a final moisture content of about 8%.

Examples 2–6 set forth various premix compositions which all were prepared on a commercial scale by the method depicted in FIG. 1 and described in part A. All the carriers used in these examples contained water, e.g., the wheat flour used contained between about 13% and about 14% water by weight.

Example 2

| Ingredients | Weight % | Weight % of final product |
| --- | --- | --- |
| Cellulase with beta-glucanase (solution) | 40% | 27.5% of dry substance |
| Wheat flour | 60% | 72.5% of dry substance |

Water content of ingredients 27%
Water content of final product 9%
(% are all by weight)

Example 3

| Ingredients | Weight % | Weight % of final product |
| --- | --- | --- |
| Cellulase with beta-glucanase (solution) | 13.9% | 8.8% of dry substance |
| Neutral protease (solution) | 3.0% | 2.1% of dry substance |
| Glucoamylase (solution) | 4.4% | 1.7% of dry substance |
| Alfa-amylase (dry) | 1.3% | 1.6% of dry substance |
| Wheat flour | 77.4% | 85.6% of dry substance |

Water content of ingredients 21%
Water content of product 9%
(% are all by weight)

Example 4

| Ingredients | Weight % | Weight % of final product |
| --- | --- | --- |
| Cellulase with beta-glucanase (solution) | 14.4% | 8.8% of dry substance |
| Cellobiase (solution) | 2.7% | 1.6% of dry substance |
| Xylanase (dry) | 0.9% | 1.1% of dry substance |
| Wheat flour | 82.0% | 88.5% of dry substance |

Water content of ingredients 18%
Water content of product 9%
(% are all by weight)

Example 5

| Ingredients | Weight % | Weight % of final product |
| --- | --- | --- |
| Cellulase with beta-glucanase (solution) | 8.2% | 5.5% of dry substance |
| Cellobiase (solution) | 8.2% | 5.5% of dry substance |
| Neutral protease (solution) | 9.5% | 6.9% of dry substance |
| Acid protease (dry) | 7.0% | 9.3% of dry substance |
| Alfa-amylase (dry) | 2.5% | 3.3% of dry substance |
| Glycoamylase (solution) | 8.2% | 3.3% of dry substance |
| Wheat flour | 56.4% | 66.2% of dry substance |

Water content of ingredients 5%
Water content of final product 9%
(% are all by weight)

Example 6

| Ingredients | Weight % | Weight % of final product |
| --- | --- | --- |
| Cellulase with beta-glucanase (solution) | 15.3% | 9.9% of dry substance |
| Neutral protease (solution) | 4.3% | 3.1% of dry substance |
| Alfa-amylase (solution) | 6.0% | 2.3% of dry substance |
| Wheat flour | 74.4% | 84.7% of dry substance |

Water content of ingredients 23%
Water content of product 9%
(% are all by weight)

The premixes of Examples 1–6 were relatively dry, thermally stable, had good flow properties, were easy to handle and can be simply and uniformly blended into a feed mix and can be prepared on a commercial scale according to the method aspect of this invention. Addition of the premixes to feed resulted in a final feed product with improved value and efficiency.

Example 7

In order to demonstrate the effectiveness of an enzyme premix, a group of broiler poultry was given feed which did not utilize the enzyme premix of this invention and comparisons were made to groups of broiler poultry which were utilizing an enzyme premix of this invention.

The results of these tests are set forth in Table 1 below.

TABLE 1

| Feed | Group I Wheat | Group II Barley Premix 1 | Group III Barley Premix 2 |
| --- | --- | --- | --- |
| Calculated energy MJ/kg feed | 12.4 | 12.4 | 12.4 |
| Weight grain (g) | 1714 | 1743 | 1693 |
| Consumption (g) | 3153 | 3195 | 3394 |
| Conversion rate | 1.84 | 1.83 | 2.00 |

In this test, each group consisted of 100 broiler chickens fed with the experimental mixes for 42 days. Group I was fed with wheat feed which did not contain any enzyme premix. Group II was fed with a barley feed which contained the enzyme premix of Example I, and Group III was fed with a barley feed which contained the enzyme premix of Example 2. Barley was chosen for this test because it is well known in the art that poultry cannot utilize barley as effectively as they can utilize wheat. Barley feed is, therefore, rarely used for chickens.

The results of the test demonstrate that the barley feed products containing the enzyme premix were effective feeds, comparable to the wheat feed which did not contain the premix. Therefore, the enzyme premix, when added to the feed during processing, increases the value and efficiency of a barley based feed and makes this feed suitable for poultry, something which heretofore was not possible.

The following general discussion and experimental examples are intended to be illustrative of the present invention, and are not to be considered as limiting. Other variations with the spirit and scope of the invention are possible and will present themselves to those skilled in the art.

We claim:

1. A thermostable premix for animal feed consisting of: a physiologically acceptable carrier capable of evenly absorbing an aqueous enzyme solution and β-glucanase and xylanase, alone or in combination with one or more enzymes taken from the group consisting of alpha-amylase, glucoamylase, cellobiase, cellulase, lipase and protease, which enzymes are not inherently thermostable at temperatures of about 70° C. or higher, said premix:
   a. being free-flowing
   b. having an even dispersion of the enzymes throughout the carrier
   c. having a water content of less than about 10% by weight
   d. retaining an effective, bioactive level of enzyme activities following processing to incorporate said premix into animal feed which utilizes temperatures of between about 70° C. to about 95° C. for between about three minutes to about thirty minutes, and subsequent pelletization.

2. The premix of claim 1 wherein said carrier is a grain flour.

3. The premix of claim 1 wherein said carrier is a barley flour.

4. The premix of claim 1 wherein said carrier is a wheat flour.

5. The premix of claim 1 wherein said carrier comprises about forty percent to about ninety-nine percent of the premix by weight, and said enzymes comprise between about one percent to about sixty percent by weight of the premix.

6. A method for producing a pelletized, free-flowing thermostable enzyme premix for animal feed which has an effective, bioactive level of enzyme activity following processing to incorporate said premix into animal feed which utilizes temperatures of between about 70° C. to about 95° C. for between about three minutes to about thirty minutes, and subsequent pelletization, which comprises the step of:

mixing a physiologically acceptable carrier capable of absorbing an aqueous enzyme solution and β-glucanase and xylanase, alone or in combination with one or more enzymes taken from the group consisting of alpha-amylase, glucoamylase, cellobiase, cellulase, lipase and protease, which enzymes are not inherently thermostable at temperatures of about 70° C. or higher, for a period of time sufficient to absorb the enzymes onto said carrier to form a carrier/enzyme complex; pelletizing said carrier/enzyme complex; and drying said pelletized carrier/enzyme complex to a moisture content of less than about ten percent by weight.

* * * * *